United States Patent [19]
Beer et al.

[11] Patent Number: 5,458,642
[45] Date of Patent: Oct. 17, 1995

[54] SYNTHETIC INTERVERTEBRAL DISC

[76] Inventors: John C. Beer; Jacqueline M. Beer, both of 820 Sycamore Ave. #185, Vista, Calif. 92083

[21] Appl. No.: 183,160

[22] Filed: Jan. 18, 1994

[51] Int. Cl.$^6$ ..................................................... A61F 2/44
[52] U.S. Cl. .................................. 623/17; 606/61
[58] Field of Search ........................... 623/16, 17, 18, 623/20; 606/61

[56] References Cited

U.S. PATENT DOCUMENTS

| | | | |
|---|---|---|---|
| 4,309,777 | 1/1982 | Patil | 623/17 |
| 4,759,769 | 7/1988 | Hedman et al. | 623/17 |
| 5,002,576 | 3/1991 | Fuhrmann et al. | 623/17 |

Primary Examiner—David Isabella
Attorney, Agent, or Firm—Bruce Garlick

[57] ABSTRACT

This invention comprises of a synthetic intervertebral disc for implantation in the human body. The disc, in its preferred embodiment, is comprised of disc-shaped plates 11(*a*&*b*) joined by springs along the inside of the outer perimeter. The plates have oval-like cutouts in their centers for a compressible polymeric core 12 to protrude from on top and bottom. The polymeric core 12 aids in the fitting of the device between the concave surfaces of two vertebrae. An elastomeric covering 14 encircles the area between the plates and is connected to the plates 11(*a*&*b*) on top and bottom to prevent body tissues from interfering with the movement of the springs 13(*a–i*). The spring system distributes forces acting on the disc between the springs and allows normal movement of the vertebrae during flexion and extension of the spine in any direction.

9 Claims, 3 Drawing Sheets

SYNTHETIC INTERVERTEBRAL DISC

BACKGROUND OF THE INVENTION

This invention relates to biological implants for human subjects. More particularly, this invention relates to a synthetic intervertebral disc that is implantable to replace a damaged intervertebral disc.

Human intervertebral discs act as cushions or shock absorbers between vertebrae. The discs include a fibrous outer layer surrounding a gel-like matrix. The fibrous outer layer contains the gel-like matrix which thereby provides the cushioning effect. As much as 500 lbs. of pressure is exerted on a single intervertebral disc when the body is in certain positions. In a single day, a natural disc may compress and extend over 13,000 times. Natural discs often deteriorate with age or are otherwise injured, causing nerves to be pinched, pain, and subsequent deterioration of the vertebral surfaces. The body continually nourishes the natural discs via nutrients from the fluid that bathes nearby tissue, but this nourishment will not repair natural discs that are significantly damaged.

When the natural discs are damaged, the physical condition created often greatly affects the mobility of the individual. Any motion of the torso causes the position of the spine to change, thereby altering the stresses on each vertebrae. The damaged disc prevents the vertebral bones from moving in natural positions and usually places pressure on surrounding tissue. Resultantly, the spinal column and the nerve roots surrounding the affected vertebral disc are often pressured by the damaged disc and the individual is usually in great pain. In some cases, the damaged disc places continual pressure on the spinal column thereby causing continuous pain.

The oldest approach to repairing severely damaged intervertebral discs, included removing the damaged natural disc and fusing the two adjacent vertebral bones into one piece. Typically, fusing the vertebral bones was performed by grafting bone between the adjacent vertebrae using metal plates and screws to hold the graft in place until it healed. Once healed, the spinal fusion prevented the vertebral bodies from moving relative to one another and relieved the pressure formerly exerted by the damaged disc on the nerve roots. However, because the procedure prevented movement that usually occurred in that section of the spinal column, patients often then suffered from painful strain on muscles, ligaments, and other tissues that surrounded the fusion. Lack of movement in the spine also put additional pressure on the discs above and below the fusion, sometimes damaging the adjacent natural discs.

Certain prosthetic structures were introduced as vertebral disc implants. Various types of polyolefin rubber, polyethylene, and silicone composites were used to create synthetic discs that mimicked the shape and structure of the natural intervertebral discs being replaced. These materials were produced to match the strength and tensile properties of a human intervertebral disc. However, with the materials currently available, the resulting synthetic discs were not durable enough to withstand the intervertebral forces and have failed soon after being implanted.

U.S. Pat. No. 4,750,769 to Hedman et. al. discloses a synthetic disc having upper and lower plates hinged together at an anterior location that are springed against each other to cause separation of the plates. However, the construction of the synthetic disc had several limitations. Most importantly, the Hedman et al. disc employed a hinge mechanism that allowed compression between adjacent vertebrae to occur only anteriorly. Such a limitation on motion allowed necessary forward flexion but did not allow posterior and lateral flexion or extension and did not allow twisting of the vertebral column at the site of the implant. Therefore, the device does not allow natural motion between the adjacent vertebrae. Further, because the implant included moving parts that were continually exposed to deposition from body tissues, their movement was limited over time and could damage adjacent body tissue. Further, because of the construction of the device, the vertebrae above and below the disc had to be cut-down to make room for the device, further traumatizing the body.

U.S. Pat. No. 4,309,777 to A. A. Patil describes a synthetic disc composed of two cups, one overlapping the other, that are held apart by springs. With this device, the cups could only move in a single dimension with respect to one another. Therefore, the springs acted only as shock absorbers between the cups. The design did not facilitate flexion of the spine in any direction. Further, because one cup slid over the other cup as the springs were compressed and because there was no lubrication between the cups, the movement between the cups was substantially inhibited by the friction between the cups. Further, body tissues such as nerves, ligaments, and muscles could become caught in the moving parts over time, damaging the tissues, and likely rendering the device incapable of movement.

SUMMARY OF THE INVENTION

It is therefore a general object of the invention to overcome the above described limitations and others of the prior prosthetic disc implants. More particularly, among other objects, it is an object of the invention to provide a synthetic intervertebral disc that is implanted between adjacent vertebrae that mimics the function of a natural disc. The disc compresses, flexes, twists, and expands in three dimensions so that the adjacent vertebrae may move relatively to one another in a natural fashion. Further, the disc provides a cushioning action between the vertebrae as does a natural disc.

To achieve these objectives, a synthetic intervertebral disc of the present invention is implantable between two vertebrae and comprises upper and lower plates, securing means, spring means between the plates, elastomeric material covering the plates, and preferably a flexible polymeric core. The upper and lower plates firmly contact the adjacent vertebrae surface and are firmly attached to the vertebrae by the securing means. The cross-sectional shape of the plates is adapted so the plates firmly attach to the vertebrae. The spring means are spaced along an outer perimeter of the upper and lower plates and connect the upper plate to the lower plate and allow limited relative motion between the upper and lower plates in three dimensions to mimic the motion allowed by the natural disc between the adjacent vertebrae.

Preferably, both plates have parallel oval cutouts in their centers to allow for a flexible polymeric core to protrude through them on top and bottom. The purpose of the core is to aid in the fitting of the device to the vertebral surfaces that are irregular and concave. Support and cushioning for the softer vertebral center is also provided by the polymeric core. The spring means preferably encircle the polymeric core to connect the plates. This placement takes advantage of the fact that the outer portion of a vertebral bone is the strongest.

The elastomeric covering then attaches to the upper and lower plates to form an enclosed volume that is impervious to bodily fluids and tissue. Thus, the spring means may operate normally within the closed volume formed by the elastomeric covering without disrupting surrounding tissue. Further, the elastomeric covering prevents the surrounding tissue from growing inbetween the sheets to inhibit the function of the disc.

The synthetic intervertebral disc is sufficiently thin so as not to require extensive cutting down of the bone during installation. The biocompatible elastomeric covering stretches and shrinks with compression and extension of the spring means and primarily serves to keep body tissues and deposits out of the moving parts of the invention. The spring means allow the plates to move in three dimensions with respect to one another to mimic the motion of a natural disc. Further, the polymeric core provides support to the disc between the adjacent vertebrae and allows the springs to cushion the motion of the vertebrae without supporting the full force between the vertebrae. Thus, the disc of the present invention fully mimics the operation of a natural disc.

These and other objects, advantages, and features of the invention will be apparent from the following description of the preferred embodiments, considered along with the accompanying drawings.

DESCRIPTION OF THE PREFERRED EMBODIMENT

Figure 1:
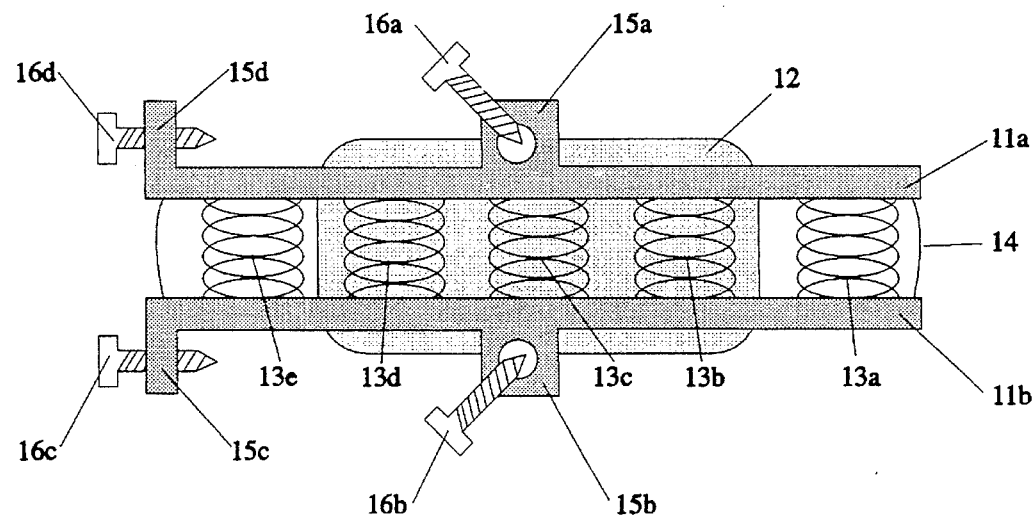
FIG. 1 is a mostly diagrammatic isolated elevational view of a synthetic intervertebral disc embodying the principles of the present invention.

A synthetic intervertebral disc embodying the principles of the present invention is shown by way of illustration in FIGS. 1–4. Referring to the FIGURES, the synthetic intervertebral disc comprises an upper plate 11a, a lower plate 11b, securing means 15, spring means 13, and an elastomeric covering 14. Preferably, the disc also includes a compressible biocompatible polymeric core 14 that extends between the plates 11a and 11b.

Both the upper 11a and lower 11b plates are preferably made of A/W glass-ceramic composite containing a dispersion of tetragonal zirconia so that they are substantially rigid. This material can be made cheaply and is bioactive. It has a bend strength of 703 MPa and a fracture toughness of 4 MPa.m$^{1/2}$ and it will form a strong bond with bone. Both plates 11(a&b) are kidney-shaped to mimic the shape of the original disc so that they firmly contact the vertebrae (17a and 17b) which they contact.

Figure 2:
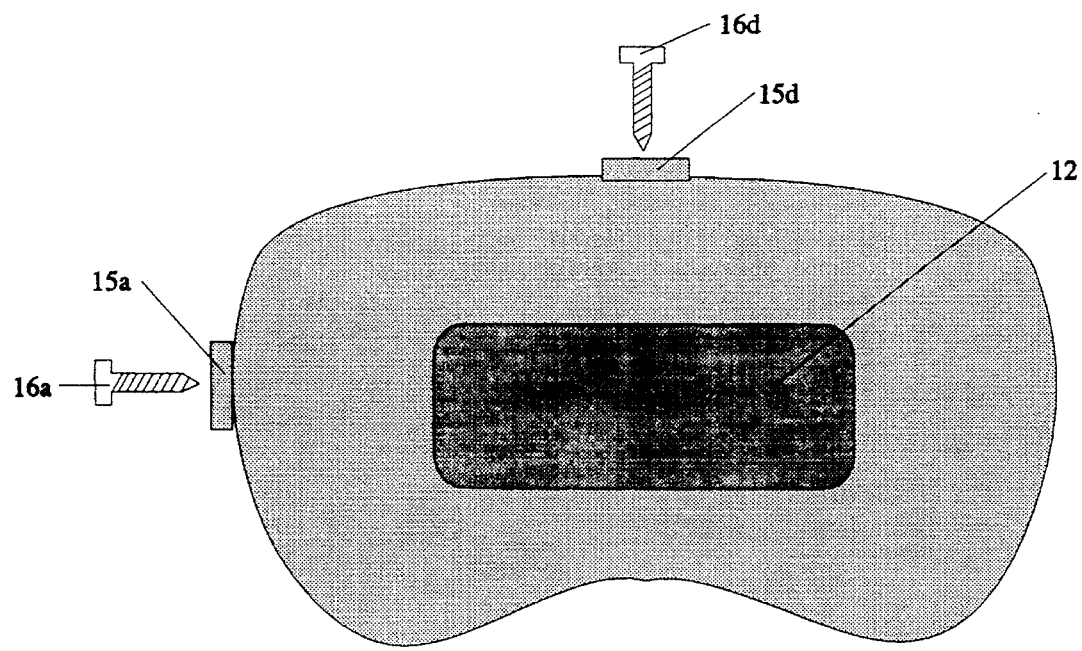
FIG. 2 is an mostly diagrammatic top view of the synthetic intervertebral disc shown in FIG. 1 detailing the upper plate.

Optionally, as detailed in FIGS. 1 and 2, the plates 11a and 11b have parallel openings in their centers to allow for the slightly compressible biocompatible polymeric core 12 to protrude through them on top and bottom. This compressible biocompatible polymeric core 12 preferably protrudes through the upper and lower plate openings into indentations in the upper and lower vertebrae. The core 12 thereby provides additional support to the vertebrae and provides a pivot upon which the vertebrae may move.

Referring again to FIGS. 1 through 4, the securing means 15 secure the upper plate 11a to the upper vertebrae 17a and the lower plate 11b to the lower vertebrae 17b. Preferably, the securing means 15 comprise a plurality of tabs (15a, 15b, 15c, and 15d) extending from edges of the plates 11a and 11b. In the preferred embodiment, each tab 15 extends substantially perpendicularly from the plate 11a or 11b so that the tabs 15 may be attached to an outer surface of the vertebrae 17a and 17b. Each tab 15a–15d connects to a vertebrae by a screw 16a–16c to hold the plates 11a and 11b firmly in place with respect to the vertebrae 17a and 17b. The screws 16(a–d) are made of a suitable titanium alloy known to those in the industry. While the illustrated embodiment uses four tabs 15a–15d with a single screw 16a–16d for each tab, one skilled in the art will readily appreciate that the same objectives may be reached in other manners. Further, the position and number of tabs 15 around the perimeter of the plates 11a and 11b can be adjusted to suit the installation and surgical approach used.

The spring means 13 is spaced along an outer perimeter of both the upper 11a and lower plates 11b and is for connecting the upper plate to the lower plate to allow limited relative motion between the upper and lower plates in three dimensions. Preferably, the spring means 13 comprises a plurality of springs (13a–13i) with each spring having a first end firmly attached to the upper plate 11a and a second end firmly attached to the lower plate 11b. Preferably, these springs 13a–13i are helical springs and made of titanium-6 aluminum-4 vanadium ELI alloy and are attached to the plates 11a and 11b during construction of the synthetic intervertebral disc. Further, preferably, the spring means 13 exerts a force between the upper 11a and lower 11b plates that is substantially equal to that of a natural disc that is being replaced. The placement of the springs 13a–13i allow the plates 11a and 11b to move relatively to one another in three dimensions just as a natural disc does.

The elastomeric covering 14 attaches to the upper 11a and lower 11b plates so as to form an enclosed volume between the upper and lower plates. This enclosed volume is impervious to bodily fluids and contains the spring means 13. In this fashion, the function of the disc remains unimpeded by the natural growth of tissue near the disc. In the preferred embodiment, the elastomeric covering 14 is made of an elastic durable material such as that used to make penal implants. While the covering 14 is shown clear to reveal the inner components of this embodiment, it may be opaque in another embodiment.

Referring particularly to FIG. 2, the shape of the upper plate 11a can be clearly seen. The cross-sectional shape of the upper plate 11a is formed so as to substantially match the cross-sectional shape of the adjacent vertebrae 17a. The lower plate 11b is formed in the same manner so as to substantially match the cross-sectional shape of the adjacent vertebrae 17b. In this fashion, maximum contact with the vertebrae 17a and 17b may be had so that maximum support will be provided and so that the plates 11a and 11b most fully fuse to the vertebrae.

Figure 3:
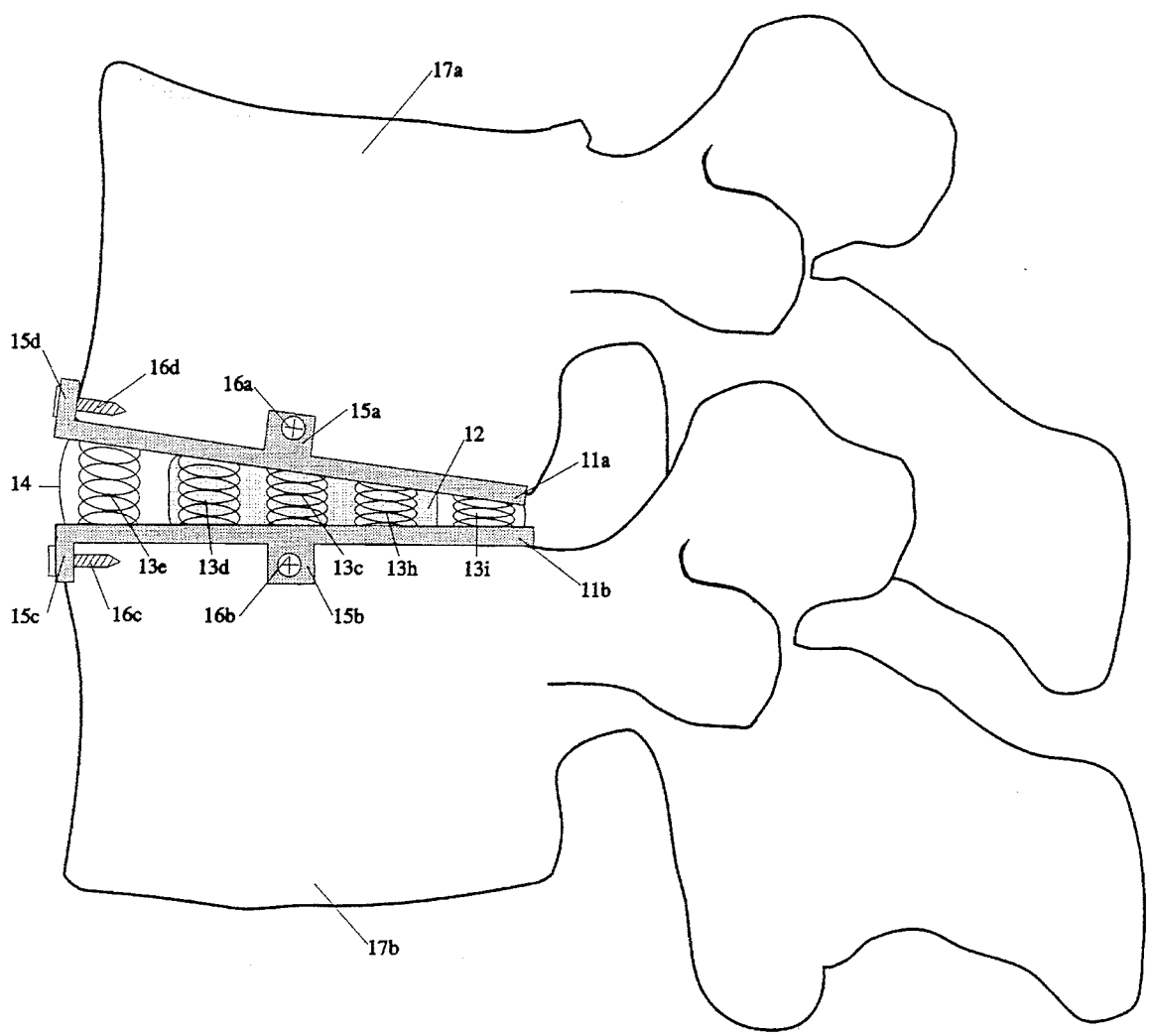
FIG. 3 is a mostly diagrammatic side-view of the synthetic intervertebral disc of FIG. 1 installed between two vertebrae with the vertebrae in an anteriorly stressed position.

FIG. 3 demonstrates the operation of the synthetic intervertebral disc during a backward bending of the spine. As is illustrated in this position, some of the springs 13h and 13i are in compression while some of the springs 13d and 13e are in expansion. The resultant forces exerted on the upper 17a and lower 17b vertebrae by the upper 11a and lower 11b plates mimic those exerted by a natural disc. The use of multiple springs 13 spreads the forces acting on the synthetic disc about the plates 11a and 11b so that no one spring endures the full force at any point in time. As is also illustrated in FIG. 3, the polymeric core 12 provides substantial support to the central portions of the vertebrae 17a and 17b so that the springs are not over-compressed.

Figure 4:
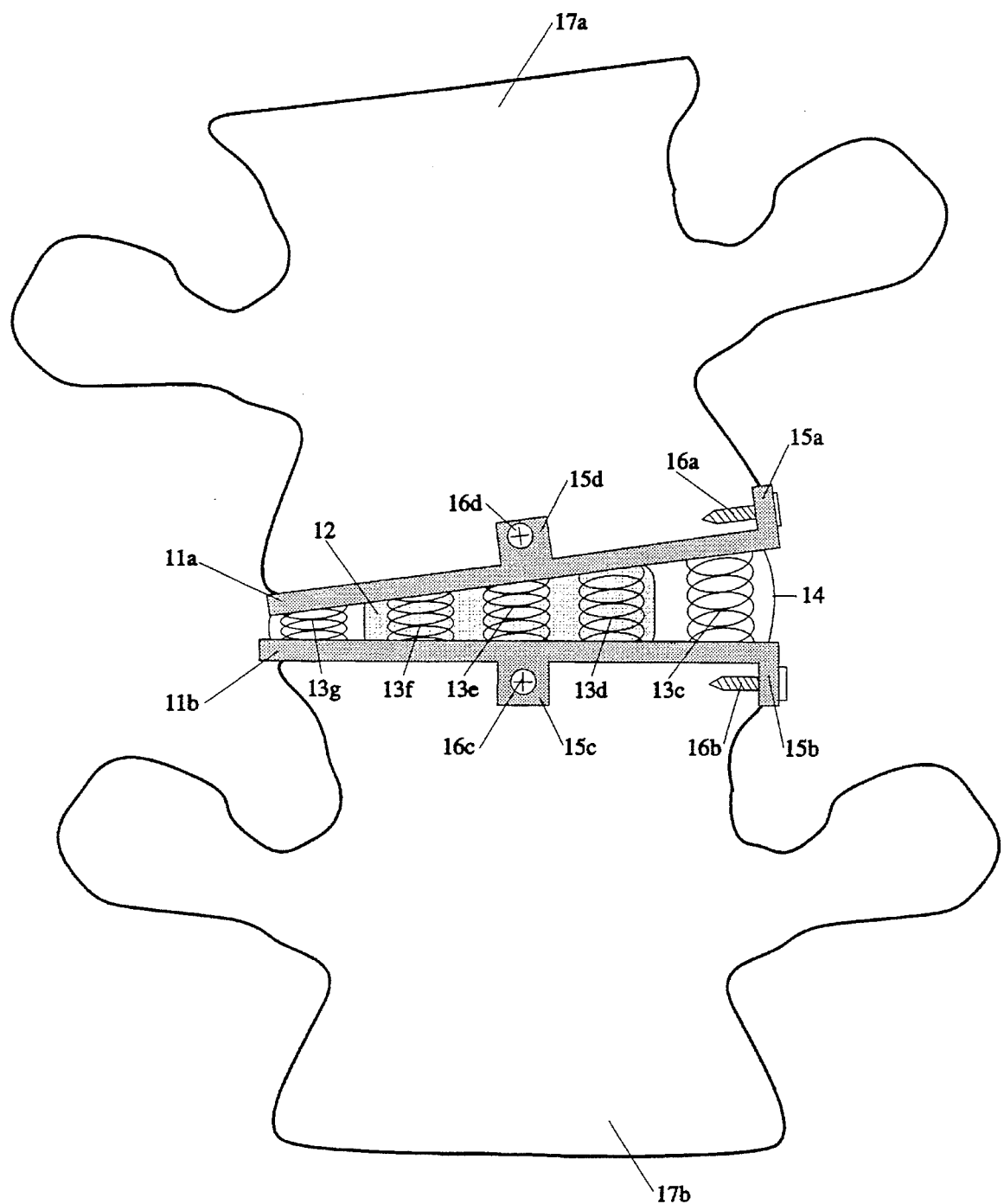
FIG. 4 is a mostly diagrammatic front-view of the synthetic intervertebral disc of FIG. 1 installed between two vertebrae with the vertebrae in a laterally stressed position.

FIG. 4 shows a frontal view of the synthetic intervertebral disc during sideways bending. In this position, the disc allows the vertebrae 17a and 17b to move relative to one another in a lateral fashion. Here also, while some of the springs 13h and 13f are in compression, others 13d and 13c are in expansion, thus allowing the disc to mimic the operation of a natural disc that has been replaced.

The above described preferred embodiments are intended to illustrate the principles of the invention, but not to limit the scope of the invention. Various other embodiments and modifications to these preferred embodiments may be made by those skilled in the art without departing from the scope of the following claims.

What is claimed is:

1. A synthetic intervertebral disc that is implantable between two vertebrae, the disc comprising:
   (a) a substantially rigid upper plate shaped to firmly contact a lower surface of an upper vertebrae;
   (b) a substantially rigid lower plate shaped to firmly contact an upper surface of a lower vertebrae;
   (c) upper plate securing means for securing the upper plate to the upper vertebrae;
   (d) lower plate securing means for securing the lower plate to the lower vertebrae;
   (e) spring means spaced along an outer perimeter of both the upper and lower plates, the spring means connecting the upper plate to the lower plate to allow limited relative motion between the upper and lower plates in three dimensions; and
   (f) an elastomeric covering attached to the upper and lower plates so as to form an enclosed volume between the upper and lower plates that is impervious to bodily fluids and that contains the spring means.

2. The synthetic intervertebral disc of claim 1 further comprising:
   (a) an opening extending through a central portion of the upper plate;
   (b) an opening extending through a central portion of the lower plate; and
   (c) a compressible biocompatible polymeric core that protrudes through the upper and lower plate openings into indentations in the upper and lower vertebrae.

3. The synthetic intervertebral disc of claim 1 wherein the securing means includes:
   (a) at least one tab extending from an edge of the upper plate, each tab connected to the upper vertebrae by at least one screw; and
   (b) at least one tab extending from an edge of the lower plate, each tab connected to the lower vertebrae by at least one screw.

4. The synthetic intervertebral disc of claim 1 wherein the spring means comprises a plurality of springs, each spring having a first end firmly attached to the upper plate and a second end firmly attached to the lower plate.

5. The synthetic intervertebral disc of claim 1 wherein the spring means exerts a force between the upper and lower plate substantially equal to that of a natural disc that is being replaced.

6. A synthetic intervertebral disc that is implantable between two vertebrae, the disc comprising:
   (a) a substantially rigid upper plate shaped to firmly contact a lower surface of an upper vertebrae and having an opening extending through a central portion of the upper plate;
   (b) a substantially rigid lower plate shaped to firmly contact an upper surface of a lower vertebrae and having an opening extending through a central portion of the lower plate;
   (c) upper plate securing means for securing the upper plate to the upper vertebrae;
   (d) lower plate securing means for securing the lower plate to the lower vertebrae;
   (e) spring means spaced along an outer perimeter of both the upper and lower plates, the spring means connecting the upper plate to the lower plate to allow limited relative motion between the upper and lower plates in three dimensions;
   (f) a compressible biocompatible polymeric core that protrudes through the upper and lower plate openings and into indentations in the upper and lower vertebrae; and
   (g) an elastomeric covering attached to the upper and lower plates so as to form an enclosed volume between the upper and lower plates that is impervious to bodily fluids and that contains the compressible biocompatible polymeric core.

7. The synthetic intervertebral disc of claim 6 wherein the spring means comprises a plurality of springs, each spring having a first end firmly attached to the upper plate and a second end firmly attached to the lower plate.

8. The synthetic intervertebral disc of claim 6 wherein the spring means exerts a force between the upper and lower plate substantially equal to that of a natural disc that is being replaced.

9. The synthetic intervertebral disc of claim 6 wherein the securing means includes:
   (a) at least one tab extending from an edge of the upper plate, each tab connected to the upper vertebrae by at least one screw; and
   (b) at least one tab extending from an edge of the lower plate, each tab connected to the lower vertebrae by at least one screw.

* * * * *